United States Patent [19]
Albert et al.

[11] Patent Number: 5,256,422
[45] Date of Patent: Oct. 26, 1993

[54] LIPID VESICLE CONTAINING WATER-IN-OIL EMULSIONS

[75] Inventors: Elizabeth C. Albert, Nashua; Donald F. H. Wallach, Hollis; Rajiv Mathur, Nashua, all of N.H.

[73] Assignee: Micro Vesicular Systems, Inc., Nashua, N.H.

[21] Appl. No.: 909,112

[22] Filed: Jul. 8, 1992

Related U.S. Application Data

[63] Continuation of Ser. No. 676,865, Mar. 28, 1991, abandoned.

[51] Int. Cl.$^5$ .............................................. A61K 9/127
[52] U.S. Cl. .................................... 424/450; 424/401; 426/602; 426/603; 428/402.2; 514/937; 514/938; 514/941; 514/943
[58] Field of Search ................... 424/401, 450, 424, 59, 424/417, 420; 514/936-943; 428/402.2; 426/603, 604, 601, 602

[56] References Cited

U.S. PATENT DOCUMENTS

| | | | |
|---|---|---|---|
| 3,957,971 | 5/1976 | Oleniacz | 424/70 |
| 4,521,440 | 6/1985 | Lansbergen | 426/602 |
| 4,743,449 | 5/1988 | Yoshida et al. | 424/420 |
| 4,793,943 | 12/1988 | Haslop | 252/135 |
| 4,895,452 | 1/1990 | Yiournas et al. | 366/173 |
| 4,911,928 | 3/1990 | Wallach | 424/450 |
| 5,061,688 | 10/1991 | Beissinger | 514/832 |
| 5,085,856 | 2/1992 | Dunphy | 424/401 |

FOREIGN PATENT DOCUMENTS

| | | |
|---|---|---|
| 2078543 | 1/1982 | United Kingdom . |
| 2079179 | 1/1982 | United Kingdom . |

OTHER PUBLICATIONS

Matsumoto, Agri. Biol. Chem. 42 739, 1978.

*Primary Examiner*—Thurman K. Page
*Assistant Examiner*—G. S. Kishore

[57] ABSTRACT

The present invention features water-in-oil emulsions having intact lipid vesicles dispersed in the water or aqueous phase. Methods of making the emulsions are also disclosed. The preferred vesicles for use in the emulsions are paucilamellar lipid vesicles, most preferably those having nonionic amphiphiles as their major structural component. The water-in-oil emulsions are useful in cosmetics, pharmaceuticals, and foods such as margarine.

12 Claims, No Drawings

LIPID VESICLE CONTAINING WATER-IN-OIL EMULSIONS

This application is a continuation of application Ser. No. 676,865, filed Mar. 28, 1991, now abandoned.

BACKGROUND OF THE INVENTION

The present invention concerns a method of making stable water-in-oil emulsions having intact lipid vesicles as part of the water or aqueous phase. These water-in-oil emulsions are primarily useful for the cosmetic industry but may also be used in other industries such as food manufacturing, e.g., the making of margarine, and pharmaceutical manufacturing.

Water-in-oil emulsions have discrete droplets of water or an aqueous solvent, called the "discontinuous phase," dispersed in a "continuous Phase" of oil. Oils useful in this type of emulsion include a broad spectrum of water-immiscible materials such as mineral oils, silicone oils, and triglycerides. Water-in-oil emulsions are distinct from oil-in-water emulsions where water forms the continuous phase and oil droplets form the discontinuous phase. Oil-in-water emulsions are more common since they are easier to establish and can be stabilized by use of many different surfactants. In contrast, water-in-oil emulsions are more difficult to establish (assuming there is a significant amount of an aqueous phase) and are often less stable. In addition, the conditions normally used to establish the water-in-oil emulsions are more rigorous than those required for oil-in-water emulsions.

Oil-in-water emulsions containing lipid vesicles have been known for many years. For example, U.S. Pat. No. 3,957,971 describes a variety of emulsions using phospholipid vesicles, i.e., liposomes, as an initial ingredient. While most of the Examples shown in this patent concern the use of suspensions of the liposomes as skin moisturizers, certain of the later Examples, particularly Examples 16 and 17, describe a hand lotion or hand cream made using these liposomes. From the description, it is unclear whether these latter Examples are water-in-oil or oil-in-water emulsions. However, it is unlikely that there are any lipid vesicles remaining because the conditions described to make the hand lotion and hand cream include high shear at high temperature, procedures which are likely to destroy any lipid vesicles.

Two United Kingdom patent applications, U.K. Patent Application Serial No. GB2079179A and U.K. Patent Application Serial No. GB2078534, concern cosmetic preparations having lipid vesicles to stabilize a water-immiscible or oily phase dispersed in an aqueous phase. These patent applications, which are assigned to L'Oreal, are specifically directed to oil-in-water emulsions rather than water-in-oil emulsions.

If any water-in-oil emulsion is deposited on the skin, the water droplets coalesce amid a film of oil. This film protects the skin from noxious agents or irritants, and helps keep the skin hydrated. Another advantage of water-in-oil emulsions is that the emulsifiers normally used in these emulsions do not cause detergent action on the skin. This is in contrast to the emulsifiers used in oil-in-water emulsions which are typically detergent-based and therefore are hygroscopic. Water-in-oil emulsions have better moisturizing properties in that they help reduce transepidermal water loss and chapping. In addition, the oil phase tends to emulsify dirt and sebum on the skin.

One possible use for water-in-oil emulsions is in a sun screen. Because these emulsions are non-hygroscopic, they do not easily take up water and thus are not easily washed off. Accordingly, they are essentially moisture-proof.

Water-in-oil emulsions also have uses outside the cosmetic area. For example, water-in-oil emulsions are used in the manufacture of margarines. U.S. Pat. No. 4,521,440, issued Jun. 4, 1985, concerns making print margarines in the form of water-in-oil emulsions with a structured lipid as the triglyceride forming the primary oil. Although this patent does not concern or suggest the use of lipid vesicles in the emulsion, there is no reason why lipid vesicles could not be used in a margarine if the materials making the vesicles are GRAS products. Further, the emulsion could be used in pharmaceutical manufacturing as well as parenteral and enteral nutrition formulas.

Accordingly, an object of the invention is to provide a method of making a water-in-oil emulsion having intact lipid vesicles as part of the emulsion.

A further object of the invention is to provide cosmetics and other useful products having water-in-oil emulsions with intact vesicles dispersed therein.

Another object of the invention is to provide a stable water-in-oil emulsion having intact non-phospholipid vesicles in the aqueous phase.

These and other objects and features of the invention will be apparent from the following description.

SUMMARY OF THE INVENTION

The present invention features a method of making water-in-oil lipid emulsions having intact lipid vesicles dispersed in the discontinuous or aqueous phase. The invention further features the emulsions themselves. These emulsions are particularly useful for use in cosmetics, e.g., skin creams, but also may have benefits in other industrial areas such as margarine and pharmaceutical manufacturing.

The water-in-oil emulsion of the invention has a continuous oil phase with a discontinuous aqueous phase dispersed therein. The discontinuous phase is in the form of droplets of water or an aqueous solvent, preferably having a diameter of about 0.1–5 mm, most preferably 0.3–3 mm. The aqueous droplets which form the discontinuous phase have intact lipid vesicles dispersed therein, preferably 1–3 vesicles per droplet.

The lipid vesicles which are dispersed in the discontinuous phase may be made of any vesicle-forming material but nonionic amphiphiles are the preferred major structural component or wall material forming the vesicles. The term "major structural component," as used herein means, includes and implies that the material is the largest lipid component (by weight) of the bilayer structure of the lipid vesicles. Preferred nonionic amphiphiles are selected from the group consisting of polyoxyethylene fatty acid esters, polyoxyethylene fatty acid ethers, diethanolamides, long chain acyl hexosamides, long chain acyl amino acid amides, long chain amino acid amines, polyoxyethylene sorbitan esters, Polyoxyethylene glyceryl mono-and diesters, glycerol mono-and distearate, glycerol mono-and dioleate, glycerol mono-and dipalmitate, and mixtures thereof.

The bilayer structure may include an ionic amphiphile in lieu of some, or all, of the nonionic amphiphile. If an ionic amphiphile is used, preferred amphiphiles are selected from the group consisting of betaines, sarcosinates, monomeric and dimeric alkyds, dimethyl distearyl amine, and mixtures thereof. Phospholipids such as lecithin or phosphotidylcholine may also be used. In addition, the emulsion preferably contains a secondary surfactant which assists in stabilizing the emulsion. The term "secondary surfactant," as used herein means, includes and implies a surfactant that is in addition to the "main structural component" of the bilayer; in fact, the "secondary surfactant" does not form part of the structure of the bilayers. Preferred secondary surfactants do not form vesicles.

The water-in-oil emulsion can include either aqueous soluble or oil soluble materials. The aqueous soluble materials can be incorporated either into the aqueous phase external to the lipid vesicles or incorporated into the lipid vesicles themselves. Similarly, any oil soluble materials can be included in the emulsion, either in the continuous phase or in the lipid vesicles. If a water-immiscible material is incorporated into the lipid vesicles themselves, the oil soluble materials may also include any materials soluble in the water-immiscible material without regard to whether they are soluble in the oil forming the continuous phase of the emulsion. These lipid vesicles which incorporate the water-immiscible materials are preferably paucilamellar lipid vesicles having the water-immiscible materials filling the central cavities. In fact, paucilamellar vesicles generally are the preferred vesicles for practicing the invention.

The oil-in-water emulsion can be used, in whole or in part, as a cosmetic composition, a pharmaceutical composition, or as an edible composition such as a margarine. Other industrial uses for water-in-oil emulsions are well known and are included in the invention.

The method of the invention forms stable water-in-oil emulsions having intact lipid vesicles incorporated in the aqueous or discontinuous phase. An aqueous phase is formed of an aqueous solvent such as water or saline, intact lipid vesicles, and a secondary surfactant. An oil phase consisting of a water-immiscible oily material is blended with the aqueous phase using gentle mixing conditions. The term "gentle mixing conditions," as used herein, means, includes and implies the equivalent of using a mixing blade or a vortex machine at about 3000 ±300 rpm for a period of about five minutes for a 100 ml volume. After blending the aqueous phase into the water-immiscible material or oil phase using these gentle mixing conditions, the force of the mixing conditions (and the speed of mixing) is increased to moderate mixing conditions. The term "moderate mixing conditions," as used herein, means, includes and implies the equivalent of mixing speeds of about 5000±500 rpm for about thirty minutes for a 100 ml volume. These moderate mixing conditions must be sufficient to transform the initial mixture into a water-in-oil emulsion but should not be sufficiently rigorous as to disrupt the lipid vesicles dispersed in the aqueous phase. After mixing, the water-immiscible material forms a continuous phase and the aqueous phase forms a discontinuous phase, with intact lipid vesicles in the discontinuous phase. The secondary surfactant stabilizes the boundary between the discontinuous phase and continuous phase. Preferably, the discontinuous phase contains discrete droplets of the aqueous phase, each droplet having a diameter of about 0.1-5 mm, preferably 0.3-3 mm. Any lipid vesicle forming materials useful to make the emulsions can be used in this method but nonionic amphiphiles are preferred. Secondary surfactants particularly useful to stabilize the emulsions include isopropyl stearate, PPG-3 myristoylether, sorbitan sesquioleate, polyoxyethylene sorbitan ethers, lauryl methicone copolyol, cetyl dimethicone copolyol, polyglyceryl-4-isostearate hexalaurate, and sorbitan esters. These secondary surfactants are normally incorporated in the oily phase.

Paucilamellar lipid vesicles, preferably paucilamellar lipid vesicles filled with an oil or water-immiscible material, are preferred for use in the method of the invention. Aqueous materials can be incorporated into the aqueous phase, either external or internal to the vesicles, while similarly oil soluble materials may be incorporated into the vesicles or external in the continuous phase. These vesicles provide flexibility for incorporating a number of different materials in the emulsions including otherwise incompatible materials.

DESCRIPTION OF THE PREFERRED EMBODIMENTS

The water-in-oil emulsions of the present invention provide improved stability and benefits for a number of products. The cosmetic area is particularly important as the water-in-oil emulsions of the invention can carry sun screens, fragrances, moisturizers, and a large variety of other materials without regard to their compatibility. The emulsion provides advantages in that the product is non-hygroscopic and can both retain and add moisture to the skin.

One major advantage of the described methods for making these emulsions is that the conditions needed to form the emulsions are rather mild. These mild conditions permit the lipid vesicles to remain intact, allowing them to act as carriers. Since the lipid material forming the bilayers acts as a protective coating between any material carried in the vesicles and the external phases, otherwise incompatible materials can be used. In certain instances, the vesicles may carry a water-immiscible solvent in a central cavity or cargo area. Using this procedure, a material which is not soluble in either the external aqueous or external oil phase but is soluble in the water-immiscible solvent can be included in the emulsion. In fact, several different types of materials can be incorporated into a single emulsion using this technique.

While any lipid vesicles could be used in the emulsions of the invention so long as they remain intact following the mild formation conditions, the preferred lipid vesicles useful in the invention are those described in U.S. Pat. No. 4,911,924, entitled "Paucilamellar Lipid Vesicles," U.S. patent application Ser. No. 410,608, entitled "Paucilamellar Lipid Vesicles Using Charge-Localized, Single-Chain Nonphopholipid Surfactants," U.S. patent application Ser. No. 598,120, entitled "Method of Making Oil-Filled Paucilamellar Lipid Vesicles," and U.S. patent application Ser. No. 654,327, entitled "Lipid Vesicles Having an Alkyd as a Wall-Forming Material." All of these patent are owned or licensed by Micro Vesicular Systems, Inc. and the disclosures of each are incorporated herein by reference. While the vesicles useful in the present invention can be made by any method, the methods and apparatus described in U.S. Pat. No. 4,895,452, entitled "Method and Apparatus for Producing Lipid Vesicles," is preferred. The disclosure of this patent is also incorporated herein by reference.

Briefly, the preferred method of the invention commences with the formation of the lipid vesicles which will be used in the emulsion. While any procedure may be used to form lipid vesicles, a preferred method commences With a lipid phase formed by blending the major structural component or primary lipid with any other lipid soluble material to incorporated into the wall structure. Sterols such as cholesterol, phytocholesterol, and similar materials which assist in modifying the thermotropic phase transitions are normal additives to this lipid phase. In addition, certain charge generating materials such as fatty acids or dicetyl phosphate may be used. The lipid phase is heated until flowing and is then blended with an excess of an aqueous phase under shear conditions such that paucilamellar lipid vesicles are formed. If an oil or water immiscible material is to be incorporated into the vesicle, it can be blended first with the lipid phase before the hydration by the aqueous phase. The mixing conditions for the aqueous phase and lipid phase are those described in U.S. Pat. No. 4,911,928, and are substantially equivalent to a relative flow rate of 5-30 m/s through a 1 mm orifice.

Once aqueous-filled vesicles are formed, they may be loaded with an oily material using the procedures described in U.S. patent application Ser. No. 598,120 or just separated for use in the emulsion. The vesicles, either loaded or unloaded, are then dispersed in the aqueous phase of the emulsion. Depending on the properties, the secondary surfactant may be included in either the aqueous or the oil phase. A separate emulsifier may also be added.

The aqueous phase is blended into the oil (or water-immiscible material) phase with gentle mixing. For example, a T-Line mixer may be used at a speed of about 3300 rpm for about five minutes at room temperature with the aqueous phase being slowly added to the oil phase. After the aqueous phase has been completely mixed with the oil phase, the stirring speed is increased to approximately 5000-5500 rpm. This moderate mixing is carried out for about thirty minutes, during which the oil phase coalesces to form a continuous phase while the aqueous phase is broken up into discrete particles forming the water-in-oil emulsion. This water-in-oil emulsion is stable and may be used for hand creams, hand lotions, and other cosmetic or non-cosmetic products.

The invention will be more clearly understood from the following, non-limiting Examples.

EXAMPLE 1

This Example shows a water-in-oil emulsion using a mineral oil as the continuous phase and a phosphate buffered saline solution containing non-phospholipid vesicles as the discontinuous phase.

First, paucilamellar lipid vesicles were made by heating a lipid phase consisting of polyoxyethylene-9 glyceryl monostearate, cholesterol, and distearyl dimethyl ammonium chloride in a 33:11:1.75 mole ratio to approximately 75° C. and blending to homogeneity. One part of this lipid phase was then hydrated with four parts of an aqueous phase consisting of 10 mM phosphate buffered saline using a syringe technique. This technique is described in more detail in U.S. Pat. No. 4,911,928. The lipid phase was heated to above the melting temperature of the lipids, in this case about 75° C., and placed in one syringe. The aqueous phase was heated to about 65° C., and was placed in the second syringe. The syringes were connected through a stopcock and the phases were mixed from one syringe to the other syringe through the stopcock for about 30 seconds to two minutes. Paucilamellar lipid vesicles having a diameter of approximately 0.5 microns were formed.

Approximately 20 ml of the lipid vesicles were suspended in 54 ml of phosphate buffered saline with an additional 1.4 g of sodium chloride added. This formed the aqueous phase for use in making the emulsion. A water-immiscible or oil phase was then made by mixing 24 ml of mineral oil (Draketex 50, Penreco) with 2 g of lauryl methicone copolyol (Dow Corning Q2-5200) and 0.5 ml of PPG-3 myristoylether, an emollient. The oil phase was placed in a Model T-Line mixer at room temperature and the aqueous phase, also at room temperature, was added slowly to the oil phase while stirring at a slow speed, approximately 3300 rpm. After five minutes of slow stirring, the stirring speed was increased to about 5500 rpm.

The resulting water-in-oil emulsion was a pourable cream. Under microscopic examination, the oil phase was clearly the continuous phase with pockets of the aqueous phase of about 2-3 mm in diameter, each containing one or more lipid vesicles.

EXAMPLE 2

In this Example, the same lipid vesicles were used as described in Example 1. About 20 ml of these vesicles were mixed with 54 ml of phosphate buffered saline and 0.1 g of sodium chloride to make the aqueous phase. The oil phase was made by blending 9.2 ml of a combination of cyclomethicone and dimethicone copolyol (Amersil ME358), 16.6 ml of cyclomethicone (Dow Corning 345 Fluid), 0.5 ml of sorbitan sesquioleate (Arlacel 83, ICI) as a secondary surfactant, and 0.5 ml castor oil.

The same conditions were used to make the emulsion as described in Example 1. The aqueous phase formed the discrete or discontinuous phase, again with droplets of approximately 2-3 mm diameter containing intact vesicles upon microscopic examination.

EXAMPLE 3

In this Example, the same lipid vesicles were used as in Examples 1 and 2 but the constituents of the aqueous phase and the oil phase were modified. The aqueous phase had approximately 20 ml of the lipid vesicles, 52 ml of phosphate buffered saline, 2.0 g of sodium chloride, and 4 ml of glycerine. The glycerine functions as a humectant. The oil phase had 2 g of lauryl methicone copolyol, 6.0 ml of cyclomethicone, 14.6 ml of mineral oil, and 1.4 ml sorbitan sesquioleate as a secondary surfactant.

The water-in-oil emulsion was made as described in Example 1. The resulting emulsion was a thick lotion.

EXAMPLE 4

This Example used the identical materials and methods as described in Example 1 except that the vesicles were "cold loaded" to include a 5% v/v of perfume. The vesicles were made using the process described in Example 1, then 19 ml of the preformed vesicles were cold loaded with 1 ml of the perfume. The perfume is a water-immiscible material. The preformed vesicles were placed in one syringe, the perfume was placed in a second syringe and the syringes were joined by a three-way stopcock. The solutions were mixed from one syringe to the other for approximately 40-50 strokes at ambient temperature. The resulting solution was then centrifuged at 3500 rpm for thirty minutes to separate the unencapsulated perfume.

These perfume-filled lipid vesicles were then used in place of the aqueous filled lipid vesicles of Example 1 to form a water-in-oil emulsion. The properties of the emulsion were substantially indistinguishable from that of Example 1, except the vesicles contain a fragrance which is released upon fracture of the vesicles.

EXAMPLE 5

In this Example, the same materials were used to form the oil phase as described in Example 3 but different vesicles were used in the aqueous phase. The vesicles were made with glycerol monostearate, cholesterol, and sorbitan monooleate in a 33:11:1.75 ratio. This lipid phase was then hydrated to form vesicles using one part of the lipid phase and four parts of a 1.5% sodium lauryl sulphate solution using the syringe method described in Example 1. After formation and separation of the lipid vesicles, they were loaded with the same fragrance, using the same "cold loading" procedure described in Example 4.

The vesicles were then used to make an emulsion following the procedures described in Example 1. The oil phase contained lauryl methicone copolyol, cyclomethicone, mineral oil, and sorbitan sesquioleate while the aqueous phase contained the vesicles, phosphate buffered saline, sodium chloride, and glycerine. The proportions used were identical to those used in Example 3.

The resulting water-in-oil emulsion was substantially indistinguishable from the emulsion described in Example 3.

EXAMPLE 6

The emulsion of this Example used the same lipid vesicles as were prepared in Examples 1-3 except they were uncharged because the disteryl dimethyl ammonium chloride was not used. These vesicles were then blended, using the same procedure as described in Example 1, with a different oil phase. The oil phase consisted of 6.25 ml of fractionated coconut oil (Miglyol 320) and 30 ml of a combination of cetyl dimethicone copolyol, polyglyceryl-4-isostearate, and hexalaurate (Abil WE09, Goldschmidt). The oil was blended with 65 ml of the uncharged lipid vesicles to form the water-in-oil emulsion. The emulsion was a thick lotion.

EXAMPLE 7

In this Example, the same vesicles used in Example 4 were blended with a different oil phase to form an emulsion. More specifically, 8.02 g of polyoxyethylene glyceryl monostearate, 1.4 g of cholesterol, and 0.08 g of dicetyl dimethyl ammonium chloride were blended and heated to 75° C. to form a lipid phase. The lipid phase was then hydrated, using the syringe technique described in Example 1, with 40 ml of a 10 mM phosphate buffered saline, at 65° C., to form the vesicles. The vesicles were cooled to room temperature and 47.5 ml of the vesicles were then blended using the cold loading technique described in Example 4 with 2.5 ml of perfume (Q2370, Quest).

An oil phase was made of 5.55 g of a mixture of cetyl dimethicone copolyol, polyglyceryl-4-isostearate, and hexalaurate, 5.55 ml of isopropylstearate, 10 ml of capric and caprylic triglycerides (Neobee M-5, Stepan), and 6.3 ml of mineral oil (Drakeol Oil 19, Penreco). This oil Phase was blended with an aqueous phase containing 20.5 ml of the perfume-laden vesicles, 57.5 ml of 10 mM phosphate buffered saline, and 0.27 g of sodium chloride using the procedure described in Example 1. The emulsion was a very thick lotion.

EXAMPLE 8

In this Example, still another type of lipid vesicle was used. The vesicles were made of 4.3 g of polyoxyethylene-4 lauryl ether (Brij 30-ICI), 1.2 g cholesterol, and 0.09 g cetyl trimethyl ammonium bromide (Sigma). These vesicles have a net positive charge. This lipid phase was heated 65° C. and hydrated with 48 ml of 10 mM phosphate buffered saline at 60° C. using the syringe method described in Example 1. The vesicles were then collected and stored for later use.

The oil phase of the emulsion was formed of 2.5 g lauryl methicone copolyol, 6.5 ml of cyclomethicone, 18.25 ml mineral oil (Drakatex 50), and 2.5 ml sorbitan sesquioleate. This oil phase was blended with an aqueous phase consisting of 17.8 ml of the lipid vesicles, 49.8 ml of 10 mM phosphate buffered saline, 5.0 ml of glycerine, and 1.75 g sodium chloride using the procedure described in Example 1. The resulting emulsion was a thick pourable lotion.

These Example are expressly non-limiting and merely illustrative of the processes and materials which can be used in the present invention. Those skilled in the art will be able to deduce other Process and materials useful in the invention. Such other processes and materials are included within the following claims.

What is claimed is:

1. A water-in-oil emulsion comprising a continuous oil phase having a discontinuous aqueous phase dispersed therein, said discontinuous phase being in the form of droplets of an aqueous medium having intact liposomes dispersed therein, said emulsion further comprising a surfactant, exterior to said intact liposomes, to assist in stabilizing said emulsion.

2. The water-immiscible emulsion of claim 1 wherein said droplets have a diameter of about 0.3-3..0 mm.

3. The water-in-oil emulsion of claim 1 wherein said liposomes comprise a nonionic amphiphiles as the major structural components.

4. The water-in-oil emulsion of claim 3 wherein said nonionic amphiphile is selected from the group consisting of polyoxyethylene fatty acid esters, polyoxyethylene fatty acid ethers, diethanolamides, long chain acyl hexasamides, long chair acyl amino acid amides, long chain amino acid amines, polyoxyethylene sorbitan esters, polyoxyethylene glyceryl mono-and diesters, glycerol mono-and disterate, glycerol mono-and dioleate, glycerol mono-and dipalmitate, and mixtures thereof.

5. The water-in-oil emulsion of claim 1 wherein said liposomes comprise an ionic amphiphile selected from the group consisting of betaines, sarcosinates, monomeric and dimeric alkyds, dimethyl distearyl amine, and mixtures thereof as the major structural component.

6. The water-in-oil emulsion of claim 1 wherein said secondary surfactant is selected from the group consisting of isopropyl stearate, polypropylene glycol, myristoylether, polyoxyethylene sorbitan ethers, lauryl methicone copolyol, cetyl dimethicone copolyol, polyglyceryl-4-isostearate hexalaurate, and sorbitan esters.

7. The water-in-oil emulsion of claim 1 wherein said liposomes comprise paucilamellar liposomes.

8. The water-in-oil emulsion of claim 7 wherein said paucilamellar liposomes comprise paucilamellar liposomes incorporating a water-immiscible compound.

9. The water-in-oil emulsion of claim 8 wherein said liposomes incorporating a water-immiscible compound further comprise an oil soluble compound to be incorporated into said emulsion.

10. A cosmetic composition comprising the water-in-oil emulsion of claim 1.

11. An margarine composition comprising the water-in-oil emulsion of claim 1.

12. A pharmaceutical composition comprising the water-in-oil emulsion of claim 1.

* * * * *